United States Patent
Hallin (10) Patent No.: US 7,738,939 B2
(45) Date of Patent: Jun. 15, 2010

(54) MULTIELECTRODE

(75) Inventor: Rolf G. Hallin, London (GB)

(73) Assignee: Uppsala Lakarkonsult AB, Stockholm (SE)

( * ) Notice: Subject to any disclaimer, the term of this patent is extended or adjusted under 35 U.S.C. 154(b) by 611 days.

(21) Appl. No.: 10/595,418

(22) PCT Filed: Oct. 13, 2004

(86) PCT No.: PCT/SE2004/001462

§ 371 (c)(1),
(2), (4) Date: Apr. 17, 2006

(87) PCT Pub. No.: WO2005/037098

PCT Pub. Date: Apr. 28, 2005

(65) Prior Publication Data

US 2007/0066876 A1    Mar. 22, 2007

(30) Foreign Application Priority Data

Oct. 17, 2003    (SE) ................................ 0302746

(51) Int. Cl.
*A61B 5/04* (2006.01)
(52) U.S. Cl. ..................... 600/393; 600/547
(58) Field of Classification Search ................. 600/393, 600/547
See application file for complete search history.

(56) References Cited

U.S. PATENT DOCUMENTS

| | | | |
|---|---|---|---|
| 3,565,060 A * | 2/1971 | Sipple .................. 600/508 |
| 3,868,947 A * | 3/1975 | Holsinger ............. 600/382 |
| 4,082,087 A * | 4/1978 | Howson ................ 600/391 |
| 4,084,583 A * | 4/1978 | Hjort ..................... 600/544 |
| 4,448,199 A * | 5/1984 | Schmid ................. 600/393 |
| 4,619,266 A * | 10/1986 | Hodgson ............. 600/393 |
| 5,255,677 A * | 10/1993 | Schaefer et al. ...... 600/384 |
| 5,353,802 A * | 10/1994 | Ollmar ................. 600/547 |
| 5,660,177 A | 8/1997 | Faupel et al. |
| 5,724,984 A * | 3/1998 | Arnold et al. ........ 600/372 |
| 5,976,094 A | 11/1999 | Gozani |
| 6,272,378 B1 * | 8/2001 | Baumgart-Schmitt ... 600/544 |
| 6,480,731 B1 * | 11/2002 | DeLuca et al. ....... 600/393 |
| 6,654,626 B2 * | 11/2003 | Devlin et al. ........ 600/383 |
| 6,865,409 B2 * | 3/2005 | Getsla et al. ......... 600/393 |
| 2003/0009096 A1 | 1/2003 | Lahteenmaki |
| 2004/0260166 A1 * | 12/2004 | Merilainen ........... 600/383 |
| 2005/0277822 A1 * | 12/2005 | Manabe et al. ...... 600/393 |

* cited by examiner

*Primary Examiner*—Lee S Cohen
(74) *Attorney, Agent, or Firm*—Brooks Kushman P.C.

(57) ABSTRACT

An embodiment of the present invention takes the form of a multielectrode for recording a bioelectrical potential difference at a detection site. The multielectrode includes a carrier that has an active electrode surface and multiple reference electrode surfaces. The multielectrode includes a plurality of recording pairs for recording the bioelectrical potential difference at the detection site multiple times in response to a single stimulus. The active electrode surface is a part of more than one of the recording pairs. The recording pairs can be coupled to processing apparatus for an improved signal-to-noise ratio of the recorded bioelectrical-potential-difference recordings.

27 Claims, 4 Drawing Sheets

MULTIELECTRODE

BACKGROUND

1. Field

Embodiments of the present invention relate to a multielectrode for recording low amplitude signals originating from bioelectrical potential differences, to a method of processing signals recorded by the invented multielectrode, to a system for recording and amplifying low amplitude bioelectrical signals, whereby an improved signal-to-noise ratio can be achieved, and to a process for manufacturing the invented multielectrode.

2. Background Art

In examinations recording bioelectrical signals, such as in ECG (electrocardiography), EMG (electromyography) and ENeG (electroneurography), the bioelectrical signals are detected and recorded by electrodes. One recording electrode, especially used in ENeG, comprises e.g. two large chlorinated silver plates or two half spherical metal surfaces, e.g. of silver, applied to a patient, in the vicinity of a nerve. The size and shape of the two electrically conducting surfaces of the electrode depend on the individual application and design, the distance between them is normally fixed, e.g. to 20-30 mm, and they may be enclosed in a plastic mould. Pieces of felt material soaked in saline or some other electrically conducting liquid are positioned in the recesses holding the electrode surfaces in order to establish contact between the electrode surfaces and the skin.

The electrically conducting surfaces constituting the electrode may also be mounted individually, directly on the skin in appropriate individual positions by using adhesive tape. When recording small amplitude signals from a peripheral limb nerve, the electrodes are positioned and fixed to the skin overlying the nerve, for example by adhesive tape or a Velcro strap attached around the electrode and the limb. The recording electrode is preferably attached to the skin with the two electrically conducting recording surfaces positioned directly above and along the nerve, minimizing the distance between the recording surfaces and the nerve.

A very high amplification is necessary in the recording system, since the amplitude of the neural signals derived from normal human limb nerves is low, between 100 and 5 microvolt. By superimposing repeated responses or by using an averaging procedure, an improvement of the signal-to-noise ratio of successively recorded nerve responses can be achieved, such that the limit for discrimination of reliable responses is around 1 microvolt.

However, there are several drawbacks with these electrodes. Due to the low amplitude of the nerve signals, the accuracy of the recording is easily disturbed. The recording procedure may have to be repeated when other simultaneously recorded potentials interfere due to e.g. sweating and movements of the patient, or when concurrent 50 Hz-disturbances occur. Since an averaging procedure is utilized, the intermittent electrical stimulation used to induce the neural activity can be prolonged, thereby causing further discomfort to the patient.

Another available technique uses near nerve recording by needle macroelectrodes. A needle macroelectrode is a needle electrode with a relatively large recording area at the tip, which is inserted percutaneously (through the skin) and brought close to or in outer contact with the nerve. A reference electrode is positioned subcutaneously nearby. Since the needle tip is located close to the activated nerve fibres in near nerve recording, the signal-to-noise-ratio is improved. In combination with averaging procedures, discrimination of signals with an amplitude of only 0.5-0.2 microvolt is possible.

In microneurography, which is another recording technique, a solid tungsten microelectrode or a concentric electrode with an outer diameter of only 200 micrometers is inserted percutaneously and positioned intraneurally. The very small surface of the active recording electrode is brought in intimate contact with nerve fibres within an individual nerve fascicle, while the reference electrode surface is positioned nearby, thereby permitting the recording of an electroneurogram of electrically induced nerve responses derived from the entire nerve fibre spectrum, i.e. from both thick and thin myelinated fibres and from thin, unmyelinated fibres, having diameters between 20-1 micrometers and conduction velocities between 70-1 msec. This is the only technique in man that also allows recording from single myelinated and unmyelinated nerve fibres in response to various natural stimuli applied within the innervation area of the impaled fascicle.

However, these procedures, using sterilized needle electrodes, are technically very demanding, time consuming and manually difficult to execute. They are, therefore, unsuitable as clinically routine diagnostic tools.

Related art is also described e.g. in U.S. Pat. No. 5,976,094.

The closest prior art is revealed in U.S. Pat. No. 5,660,177, disclosing a bioelectrical sensing electrode comprising an array of electrodes, by which the DC-potential can be recorded at several different detection sites on a patient, in order to screen e.g. a breast, (see e.g. FIG. 1 and column 5, lines 32-60). Prior art is also disclosed in US 2003/009096, which describes a sensor system for measuring bioelectrical potentials on different detection sites on the head of a patient, by using an array of three electrodes. In all techniques described in these prior art documents, the biological signal of interest is recorded only one time at the detection site. By contrast, embodiments of this invention provide for an improved recording of bioelectrical potential differences derived from the same bioelectrical impulse generator/s/, e.g. nerve fibre/s/ or muscle fibre/s/ at only one detection site, with improved signal-to-noise ratio achieved by using multiple recordings and a summation of the bioelectrical potential differences derived from said impulse generators at this detection site, using several recording pairs, which are provided on one electrode.

An object of embodiments of this invention is to limit or eliminate some of the described problems when recording low amplitude bioelectric signals and to provide an improved non-invasive recording electrode and a novel procedure to process the recorded signals, whereby in particular the signal-to-noise ratio of the signals is improved compared to prior techniques, making embodiments of the invention suitable for clinical examinations of patients.

SUMMARY

The above object is achieved by the multielectrode, by the recording method, by the recording system and by the manufacturing process according to the attached claims, which are hereby incorporated in their entirety.

The claims are directed to a multielectrode comprising a carrier provided with separate electrode surfaces for improved recording of the bioelectrical potential difference/s/ at one detection site. Said separate electrode surfaces include one or more active electrode surfaces and two or more reference electrode surfaces for providing two or more recording pairs, each of said active electrode surfaces participating in more than one of said recording pairs for recording said bioelectrical potential difference/s/ multiple times at the same detection site. The recording pairs are adapted to be connected to processing apparatus comprising inversion apparatus and summation apparatus to provide an improved signal-to-noise ratio of said recorded potential difference/s/.

The active electrode surfaces may be centrally positioned on the surface area of the carrier and the reference electrode surfaces may be symmetrically positioned between the active electrode surfaces and the edge delimiting the surface area of the carrier.

The carrier may consist of two or more separate sub-carriers, of which each sub-carrier is provided with at least one separate electrode surface, the total number of electrode surface being at least three.

The active electrode surfaces may all have a substantially similar size and shape and the reference electrode surfaces may also have a substantially similar size and shape. The size and/or shape of the reference electrode surfaces may be substantially similar to or substantially different from the size and/or shape of the active electrode surfaces. The surface of the carrier may be provided with elevated parts to which electrode surfaces are attached, or with recesses into which electrode surfaces are fitted, and the electrode surfaces may extend on the sides of the elevated parts or of the recesses in the carrier.

The recesses in the carrier may be delimited by vertical edges elevated from the surface of the carrier, thereby preventing short-circuiting between adjacent electrode surfaces.

Electrically conducting material may be attached to at least some of the electrode surfaces.

The carrier and/or the electrode surfaces may be provided with an adhesive for attaching the multielectrode to the detection site.

The carrier with the electrode surfaces may be formed by one or more thin layer/s/of an insulating material provided with a pattern of electrode surfaces.

The carrier may be provided with three or more sterilized needles, of which each needle tip constitutes at least part of an electrode surface.

The claims are also directed to a method of processing signals indicating bioelectrical potential differences at a detection site, the signals recorded by the multielectrode according to the invention, the method comprising a summation of the signals recorded at the detection site by at least two recording pairs, said signals derived from generators of bioelectrical potential differences.

An inversion of at least one of the signals may be performed prior to the summation.

A delay from the starting point of the induced response may be performed before the summation, and at least part of one or more signals may be muted prior to the summation.

The claims are also directed to a process of manufacturing said multielectrode, at least part of the process being manual, or at least part of the process being performed by mechanical manufacturing apparatus. The steps may comprise the manufacturing of thin layers of an insulating material, providing some of the layers with patterns of electrode surfaces and folding, fastening and/or gluing the layers together.

The claims also relate to a system for recording signals indicating bioelectrical potential differences at a detection site, the system comprising at least one multielectrode and processing apparatus connected to said multielectrodes, the processing apparatus comprising summation apparatus and inversion apparatus.

The processing apparatus may further comprise delay apparatus and muting apparatus.

Other features and further advantages of the invention will be apparent from the following description and the described nonlimiting embodiments of the invention.

BRIEF DESCRIPTION OF THE DRAWINGS

Embodiments of the present invention will be described in more detail and with reference to the drawings, of which.

DESCRIPTION OF EMBODIMENTS OF THE INVENTION

One object of embodiments of the invention is to improve the recording of low amplitude bioelectric signals originating from generators of bioelectrical potential differences, i.e. from nerve fibers or motor units. This is accomplished by the invented electrode, comprising a plurality of separate recording surfaces, by the invented processing method, by the invented system and by the invented manufacturing process.

Figure 1:
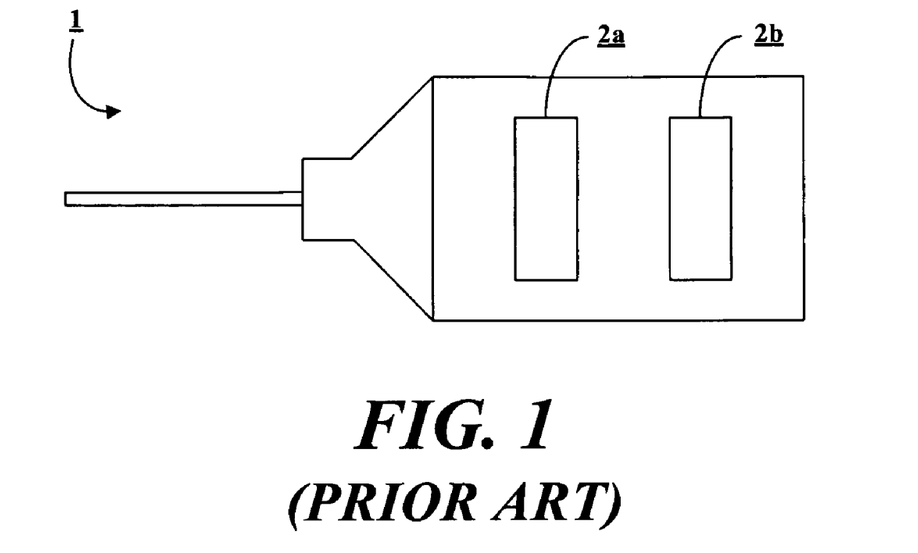
FIG. 1 illustrates a top view of a presently used macroelectrode.

FIG. 1 illustrates one prior art macroelectrode 1, provided with two electrode surfaces 2a and 2b of an electrically conducting material, preferably a metallic material. The size of the prior art macroelectrode is approximately 1 cm×2.5 cm×5 cm, and the size of each of the two electrode surfaces is approximately 6 mm×20 mm. The macroelectrode is intended to be fixed to the skin overlying a nerve with the electrode surfaces facing the skin.

Figure 2:
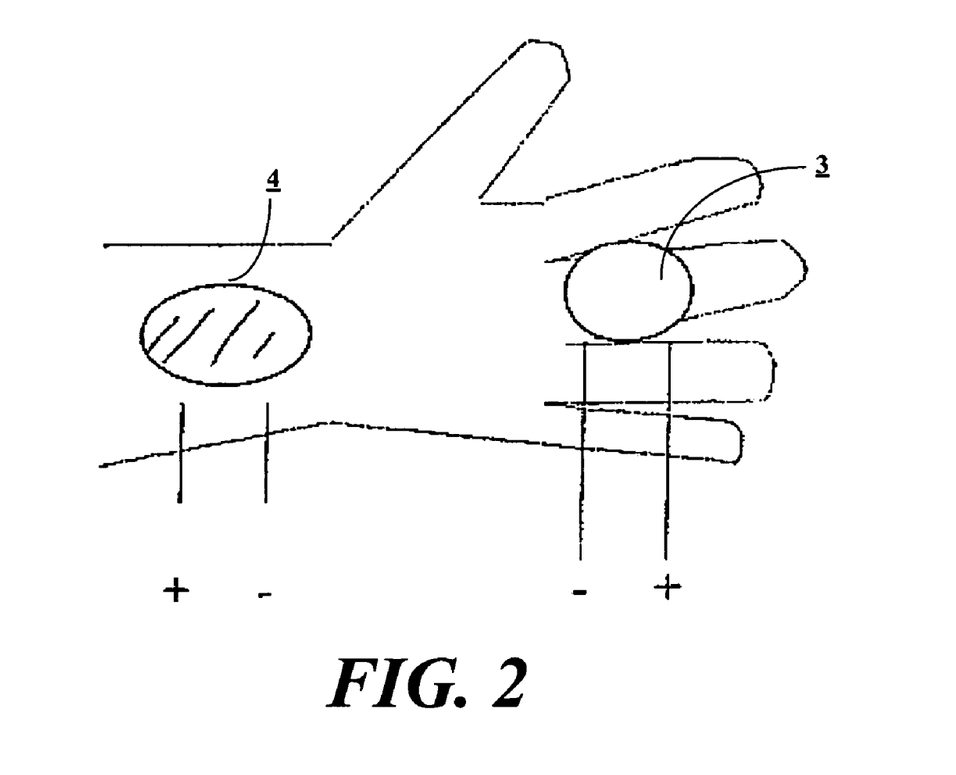
FIG. 2 illustrates an arrangement for recording electrically evoked neural activity.

FIG. 2 schematically illustrates an arrangement for recording neural activity in a large number of nerve fibers located in a peripheral nerve at the wrist of a patient. In this arrangement, the bioelectric neural activity is evoked by repetitive electrical shocks applied to the patient at a stimulation site 3 located on one of the patient's fingers. However, bioelectrical activity may alternatively be evoked by magnetic, physical or natural stimulation, such as e.g. by skin stimulation and, in other arrangements, by voluntary muscle contractions, light flashes or sounds. A bioelectrical signal between two spots on the skin of the patient, caused by the evoked neural activity, is detected by a recording electrode attached to the patient at a detection site 4 located on the wrist of said patient. The arrangement is further provided with appropriate electrical grounding apparatus, which is not illustrated in this figure. The signals recorded by the electrode are processed electronically in order to obtain an optimal signal to be displayed, e.g. on an oscilloscope.

When recording bioelectrical signals in an animal, the detection site may be on the skin of the animal, or alternatively in a paraffin filled pool limited by skin flaps where the electrode surfaces are submerged to contact a nerve or some other generator of bioelectrical potential differences in the animal, e.g. a nerve root. The electrode surfaces in the pool may be located in intimacy or close to the top or underneath said generator.

In order to improve the signal-to-noise-ratio of recorded bioelectrical potential differences at a detection site, which e.g. is located on the skin directly overlying a nerve of a patient, the novel electrode according to embodiments of this invention comprises a carrier provided with a plurality of separate electrode surfaces. The electrode surfaces include one or more active electrode surfaces to be attached to the skin at a central part of the detection site, and two or more reference electrode surfaces to be attached to the skin at a small distance from the center of the detection site. The active electrode surfaces are preferably centrally positioned on the electrode carrier and the reference electrode surfaces are preferably positioned between the active electrode surfaces and the edge of the surface area of the carrier, the localization depending on the shape and size of the carrier. The reference electrode surfaces may be grouped, so that the groups located on the carrier symmetrically surround the active electrode surface or surfaces.

The recording of a potential difference, i.e. a bioelectrical signal, is achieved by pairs of electrode surfaces, one active (negative) and one reference (positive) electrode surface, constituting one recording pair between which the potential difference is detected. By using multiple electrode surfaces, the bioelectrical potential difference/s/ occurring at one detection site can be detected multiple times, by several recording pairs at this site, with the active electrode surface/s/participating in more than one recording pair. However, the present disclosure further contemplates that the bioelectrical potential difference/s/ occurring at one detection site may be determined multiple times using at least one active electrode surface and at least one reference electrode surface. The present disclosure further contemplates that the bioelectrical potential difference/s/ occurring at one detection site may be detected multiple times using at least one active electrode surface and a first and second reference electrode surface. Processing apparatus connected to the multielectrode, including an inversion and a summation unit, adds the recorded values of the bioelectrical potential differences detected by each recording pair, of which at least one of the values may be inverted before summation, thereby achieving an improved recording of the bioelectrical signal, i.e. regarding the signal-to-noise-ratio.

The number of active electrode surfaces provided on a multielectrode is one or more and typically between one and three. The number of reference electrode surfaces is two or more and typically between four and twenty.

The electrode surfaces of one multielectrode may have different shapes and sizes. However, if the electrode surfaces have similar shape and size, their electrical impedance is similar, which may be advantageous. According to one embodiment of the invention, all of the active electrode surfaces of one multielectrode have similar shape and size and all of the reference electrode surfaces have similar shape and size, while the size and shape of the reference electrode surfaces is different from the shape and size of the active electrode surfaces, or, alternatively, only the shape is different while the size of all of the electrode surfaces is similar.

Figure 3:
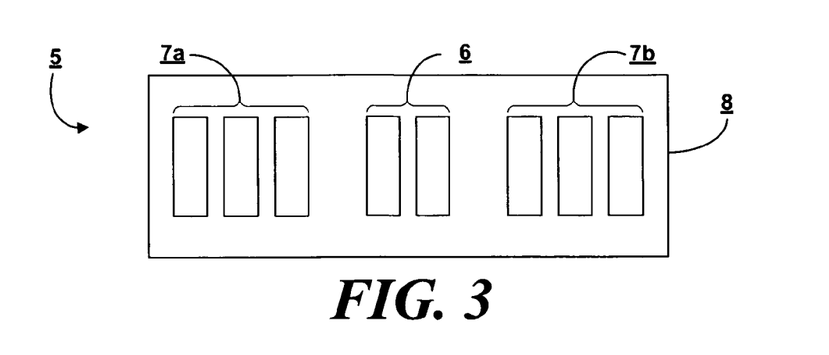
FIG. 3 is a top view of a first embodiment of the invented multielectrode.
Figure 4:
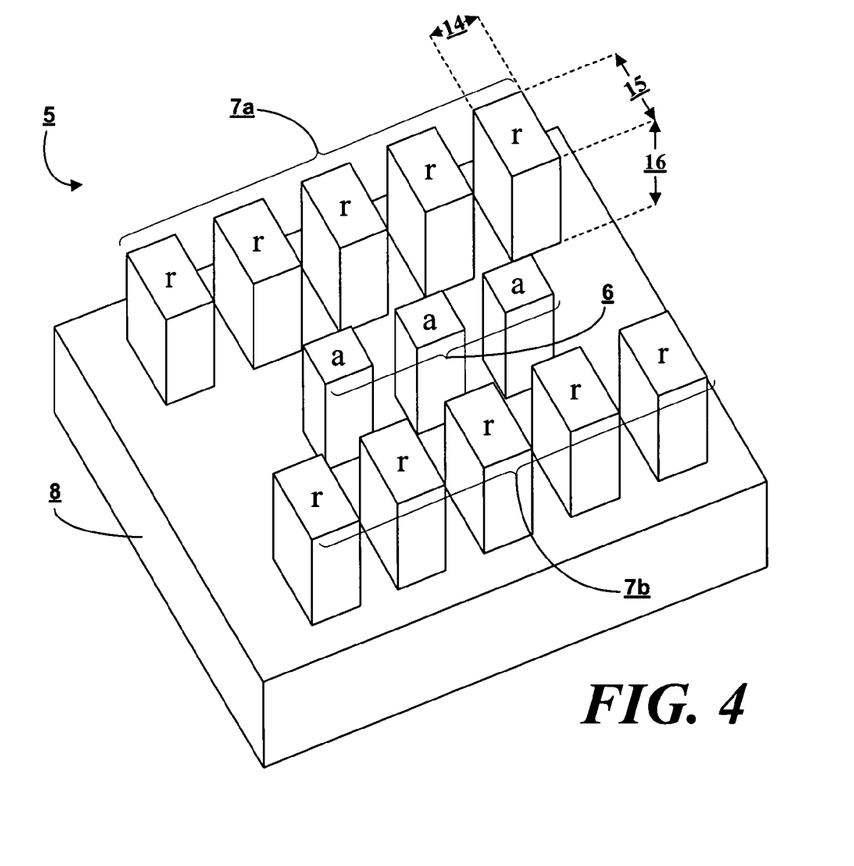
FIG. 4 is a perspective view of a second embodiment of the invented multielectrode.
Figure 5:
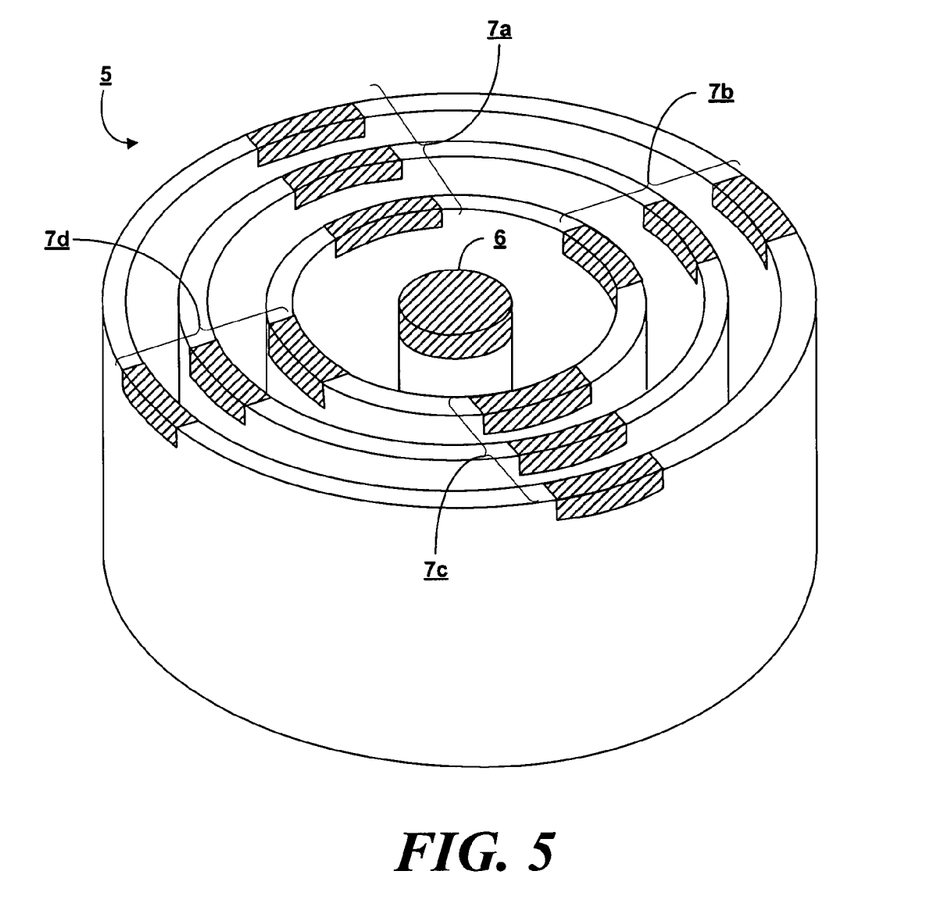
FIG. 5 is a perspective view of a fourth embodiment of the invented multielectrode.

FIGS. 3-5 show top views of exemplary embodiments of the invented multielectrode, provided with a multitude of separate electrode surfaces. The potential difference at a detection site is detected and measured by several recording pairs, each recording pair consisting of one of the active electrode surfaces and one of the reference electrode surfaces of the multielectrode. The recorded values are processed and summed, achieving an improved recording of a bioelectrical signal.

FIG. 3 illustrates a first embodiment of the invented multielectrode 5, having a rectangular electrode carrier 8, on which rectangular electrode surfaces are attached. The electrode, according to this exemplary embodiment, is provided with one group 6 of two active electrode surfaces, and with two groups, 7a and 7b, each with three reference electrode surfaces, the two groups positioned on either side of the group of active electrode surfaces 6. The multielectrode is intended to be applied to a patient with the active electrode surfaces located directly overlying the detection site, e.g. in a nerve of a patient. If the rectangular electrode carrier is positioned along the stretch of the nerve, the stretch of an individual, rectangular, electrode surface is perpendicular to the longitudinal stretch of the nerve.

FIG. 4 illustrates a second embodiment of the invented multielectrode 5, having a more quadratic configuration of the electrode carrier 8, to which separate electrode surfaces are attached. The multielectrode according to this second, exemplary, embodiment is provided with one group, 6, of three substantially quadratic active electrode surfaces and with two groups, 7a, 7b, each with five rectangular reference electrodes. In this embodiment, the three groups of electrode surfaces are located in parallel on the carrier, the group of active electrode surfaces located in between the two groups of reference electrode surfaces and intended to be located directly above the stretch of the nerve.

According to a third, not illustrated, embodiment of the invented multielectrode, the configuration of the multielectrode carrier 8 comprises two or more separate sub-carriers, intended to be individually applied to the detection site 4 of a patient.

Each sub-carrier is provided with one or more separate electrode surfaces, of which the active electrode surfaces preferably are positioned on the same sub-carrier. The total number of electrode surfaces must be three or more.

FIG. 5 illustrates a fourth, exemplary embodiment of the invented multielectrode 5, having a circular electrode carrier 8, on the elevations of which separate electrode surfaces are attached. The multielectrode is provided with only one, centrally located, active electrode surface 6 and four groups, 7a, 7b, 7c, 7d, of reference electrode surfaces, each with three reference electrodes, these four groups surrounding the active electrode surface and positioned with approximately 90 degrees angular distance from each other. The carrier surface of this embodiment may have e.g. a circular, semicircular, semiellipsoid, partly rectangular or partly square extension. According to an alternative embodiment, the electrode surfaces are attached into recesses in this type of electrode carrier.

A multielectrode according to FIG. 5 is mainly intended for recording of signals in a detection site from which signals are spread uniformly, which occurs e.g. when obtaining precordial leads of ECG-recordings or in surface EMG-recording.

The size of the carrier of the invented multielectrode may vary considerably depending on the application of the multielectrode, but a rectangular carrier, according to the embodiment illustrated in FIG. 3, may have an approximate length of e.g. 5 cm, a width of e.g. 2.5-3.5 cm and a thickness of e.g. 1-1.5 cm.

The electrode surfaces may be attached in the bottom of recesses in the carrier, the recess having a depth of e.g. 10 mm, a length of e.g. 20 mm and a width of e.g. 2-4 mm. The electrode surfaces may extend on the sides of the recess. Alternatively, the electrode surfaces may be attached, e.g. glued, on elevated parts of the surface of the carrier, the elevated parts having a height of approximately up to 10-15 mm, a length of e.g. 10 mm and a width of e.g. 1.5 mm. The electrode surfaces may extend on the sides of the elevated parts.

Part of an electrode surface may be unexposed due to insulating material covering part of the surface.

The individual size of an exposed or unexposed electrode surface depends on the application, but is typically between 40-150 mm2. However, the electrode surface may be as small as a few mm2 and larger than 200 mm2.

By extending the electrode surfaces on the side of recesses or on elevated parts of a carrier, a larger electrode surface area is possible, whereby e.g. a lower impedance can be achieved.

The distance between adjacent electrode surfaces, i.e. the interelectrode distance, may vary according to the application, the size of the carrier and the size and shape of the electrode surfaces, but may typically be between 1 mm and 2 mm. However, by varying the interelectrode distance, various degrees of packing and/or grouping of active and of reference electrode surfaces can be achieved.

The distance between the electrode surfaces of one recording pair depends e.g. on the size of the electrode carrier and the location of the reference electrodes in relation to the active electrodes. It is normally between 12 mm and 20 mm, but may be shorter or longer. The variations in the distances between the electrode surfaces constituting the recording electrode pairs on one multielectrode is, however, preferably less than 5 mm.

Electrically conducting material, such as e.g. a gel or a moist absorbing fabric or felt soaked in e.g. saline, may be attached to the electrode surfaces in order to establish the contact between the electrode surface and the skin. The attachment may be achieved e.g. by pressing the electrically conducting material into recesses or wrapping it around elevations and holding it in place by plastic pieces or by appropriately adopted o-rings.

The carrier and/or the electrode surfaces may be provided with an adhesive in order to secure the attachment of the electrode to the skin of the patient.

The electrode surfaces are electrically insulated from each other by plastic, mould or by air, and are individually connected to shielded conductors within a cable, which feeds the obtained signals from a recording pair individually into the processing apparatus.

Recesses in the carrier may be delimited by thin, vertical edges elevated from the horizontal surface of the carrier, thereby preventing short-circuiting between neighboring electrode surfaces placed in said recesses.

According to another embodiment of the invented multielectrode, the multielectrode is manufactured in a thin version, as a stick-on electrode, adapted to be fastened to the skin of a patient with adhesive tape. For example, with reference back to FIG. 3, the multielectrode 5 may be manufactured so that the carrier 8 may be formed by one or more thin layer/s/ of mould of semi-elastic plastic. The multielectrode 5 may further be formed so that various patterns of active and passive electrode surfaces 6, 7a, and 7b, may be positioned within carrier 8 so that each electrode surface is electrically separated by the insulating layers. Although FIG. 3 illustrates the active and passive electrode surfaces 6, 7a, and 7b substantially within the edges of the carrier 8, the present disclosure contemplates that at least a portion of the active and passive electrodes 6, 7a, and 7b may extend beyond the edges of the carrier 8. By cutting and/or folding the one or more carrier 8 layer/s/ and gluing them together, flat multielectrodes of different design may be achieved.

According to another embodiment of the invented multielectrode, the carrier is provided with three or more needles of which the needle tip constitutes an electrode surface, or part of an electrode surface. Such a sterilized multielectrode is adapted to penetrate the skin of a patient. For example, with reference to FIG. 4, the reference electrodes 7a, 7b and the active electrodes 6 are elevated away from the carrier 8. One or more of the elevated active and reference electrodes 6, 7a, 7b may be formed so as to include a needle tip adapted to penetrate the skin of a patient.

The signals from the recording pairs of the multielectrode are fed to processing apparatus, connected to the multielectrode, and summed in summation apparatus, thereby achieving the desired improved signal-to-noise-ratio. The recordings from different recording pairs can have different polarity. However, a common polarity is preferably defined in the processing apparatus and an inversion of some of the recordings is performed before the summation.

If the bioelectrical signal is evoked by repetitive electrical stimulation and recorded by a large number of recording pairs, the electrical stimulation signal, i.e. the stimulus artifact, which precedes the nerve response, may cause a saturation of the summation unit, thereby distorting the recording. This can be avoided by providing delay apparatus, whereby a canceling of the stimulus artefact can be accomplished by inverting some recorded signals with a delay after the artefact, thus inverting only the neural response and not the corresponding artefact. Alternatively, the parallel amplifiers connected to the summation unit may be muted for the duration of the electrical stimulus, thereby providing muting arrangements. Also, in some cases some of the nerve responses must be inverted before summation.

Figure 6:
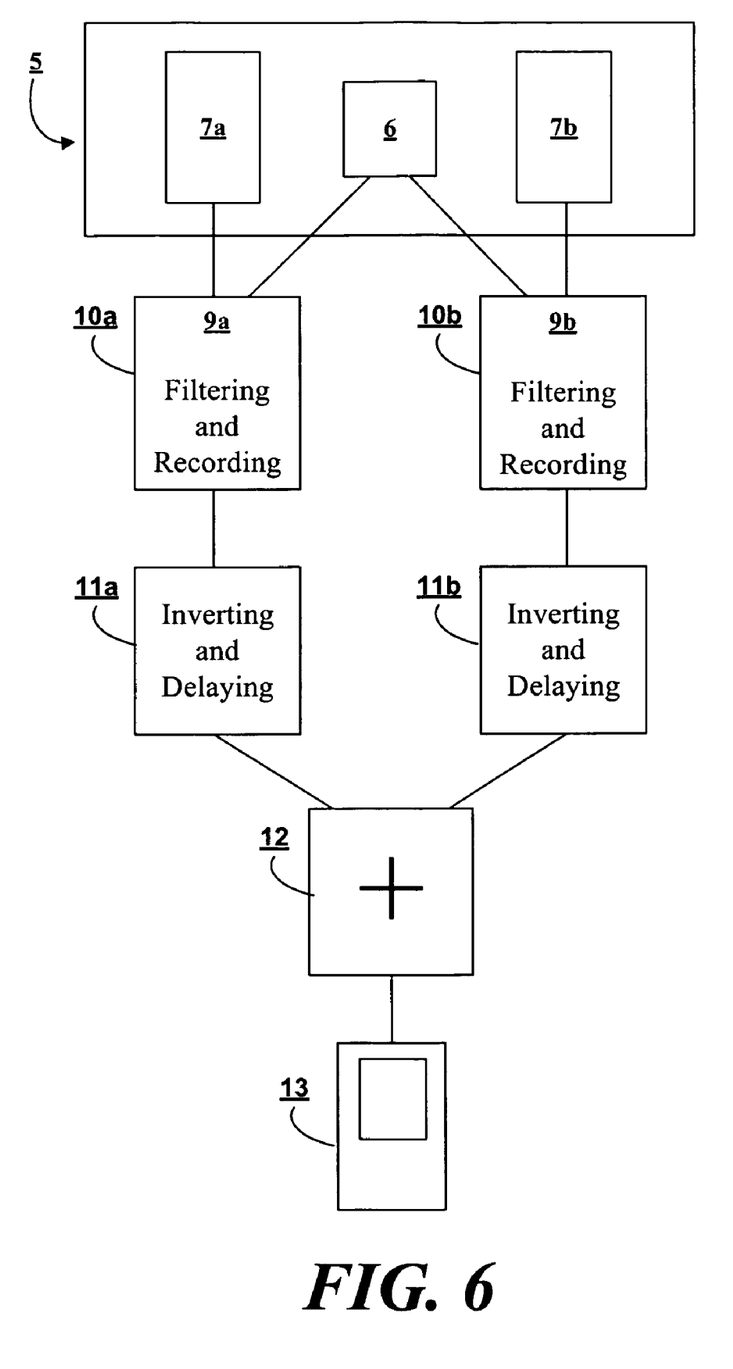
FIG. 6 is a block diagram illustrating one method of processing bioelectric signals recorded by the invented multielectrode.

FIG. 6 is a block diagram illustrating one method of processing signals recorded by one embodiment of the invented multielectrode 5, which is only provided with one active electrode surface 6 and two reference electrode surfaces 7a, 7b. Bioelectrical potential differences in the skin overlying a nerve of a patient are detected and measured by two recording pairs 9a, 9b, of which 9a consists of electrode surfaces 6 and 7a and 9b consists of electrode surfaces 6 and 7b. The recording pairs are connected to amplifying and filtering apparatus 10a, 10b, from which the output signals are fed to inverting and delaying apparatus 11a, 11b. The output signals from the inverting and delaying apparatus are connected to summation apparatus 12. The summed signals are, subsequently, displayed by display apparatus 13, which may comprise e.g. a personal computer or an oscilloscope.

The multielectrode, may be manufactured by suitable e.g. mechanical manufacturing apparatus, and part of the manufacturing process may be manual. A substantially flat multielectrode may be manufactured by fastening together, e.g. by glue, thin layer/s/ of very thin plastic or other insulating material, of which some of the layer/s/ are provided with various patterns of electrode surfaces.

Thus, by the described multielectrode comprising a plurality of separate recording surfaces, by the parallel processing of the signals recorded by the multielectrode, by the system comprising the multielectrode and processing apparatus and by the manufacturing of these items, an improved recording of low amplitude bioelectric signals, originating from bioelectrical potential differences, can be accomplished.

The invention is not restricted to the described embodiments in the figures, but may be varied freely within the scope of the attached claims.

The invention claimed is:
1. A multielectrode for measuring a low amplitude bioelectrical signal at a detection site, the multielectrode comprising:

a carrier including at least one active electrode surface and at least a first and a second reference electrode surface; and a processor in electrical communication with the carrier, the processor configured to:

receive the low amplitude bioelectrical signal using the at least one active electrode surface and the at least first reference electrode surface, wherein the low amplitude bioelectrical signal is received in response to an applied bioelectrical stimulus signal;

determine an evoked first bioelectrical potential difference a plurality of times, wherein the evoked first bioelectrical potential difference is based upon the low amplitude bioelectrical signal received using the at least one active electrode surface and the at least first reference electrode surface;

receive the low amplitude bioelectrical signal using the at least one active electrode surface and the at least second reference electrode surface, wherein the low amplitude bioelectrical signal is received in response to the applied bioelectrical stimulus signal;

determine an evoked second bioelectrical potential difference a plurality of times, wherein the evoked second bioelectrical potential difference is based upon the low amplitude bioelectrical signal received using the at least one active electrode surface and the at least second reference electrode surface; and sum the plurality of evoked first bioelectrical potential differences and the plurality of evoked second bioelectrical potential differences in order to increase the signal-to-noise ratio of the low amplitude bioelectrical signal.

2. The multielectrode of claim 1, wherein the processor is further configured to:

delay the recording of the first bioelectrical potential differences during the period of time that the bioelectric stimulus signal is applied.

3. The multielectrode of claim 2, wherein the processor is further configured to:

invert at least one of the plurality of first bioelectrical potential differences recorded.

4. The multielectrode of claim 3, wherein the processor is further configured to:

delay the recording of the second bioelectrical potential differences during the period of time that the bioelectric stimulus signal is applied.

5. The multielectrode of claim 4, wherein the processor is further configured to:

invert at least one of the plurality of second bioelectrical potential differences recorded.

6. The multielectrode of claim 1, wherein the at least one active electrode surface is substantially positioned in a central location on the carrier.

7. The multielectrode of claim 1, wherein each reference electrode surface is symmetrically positioned between the active electrode surface and an edge delimiting the surface area of the carrier.

8. The multielectrode of claim 1, wherein the size and shape of at least one of the reference electrode surfaces is substantially different from the size and shape of the active electrode surface.

9. The multielectrode of claim 1, wherein the carrier is formed of at least three sterilized needles, each needle tip constituting at least a portion of each respective electrode surface.

10. The multielectrode of claim 1, wherein the carrier further includes an insulation material which electrically insulates each of the respective electrode surfaces.

11. The multielectrode of claim 1, wherein the size and shape of the active and reference electrode surfaces is substantially similar so that the electrical impedance is substantially similar.

12. A multielectrode for measuring a low amplitude bioelectrical potential difference at a detection site, the multielectrode comprising:

a carrier including at least one active electrode surface and at least a first and a second reference electrode surface; and a processor in electrical communication with the carrier, the processor configured to:

receive a first low amplitude bioelectrical signal using the at least one active electrode surface and the at least first reference electrode surface, wherein the first low amplitude bioelectrical signal is received in response to an applied bioelectrical stimulus signal;

determine an evoked first bioelectrical potential difference a plurality of times, wherein the evoked first bioelectrical potential difference is based upon the first low amplitude bioelectrical signal received using the at least one active electrode surface and the at least first reference electrode surface;

amplify and filter the plurality of first bioelectrical potential differences;

invert at least one of the plurality of first bioelectrical potential differences;

record the plurality of first bioelectrical potential differences;

receive a second low amplitude bioelectrical signal using the at least one active electrode surface and the at least second reference electrode surface, wherein the second low amplitude bioelectrical signal is received in response to the applied bioelectrical stimulus signal;

determine an evoked second bioelectrical potential difference a plurality of times, wherein the evoked second bioelectrical potential difference is based upon the second low amplitude bioelectrical signal received using the at least one active electrode surface and the at least second reference electrode surface;

amplify and filter the plurality of second bioelectrical potential differences;

invert at least one of the plurality of second bioelectrical potential differences;

record the plurality of second bioelectrical potential differences; and sum the plurality of evoked first bioelectrical potential differences and the plurality of evoked second bioelectrical potential differences in order to increase the signal-to-noise ratio of the low amplitude bioelectrical signal.

13. The multielectrode of claim 12, wherein the processor is further configured to:

delay the recording of the plurality of first bioelectrical potential differences during the period of time that the bioelectric stimulus signal is applied.

14. The multielectrode of claim 13, wherein the processor is further configured to:

delay the recording of the plurality of second bioelectrical potential differences during the period of time that the bioelectric stimulus signal is applied.

15. The multielectrode of claim 12, wherein the carrier further includes elevated portions to which each of the respective electrode surfaces are coupled.

16. The multielectrode of claim 15, wherein at least one of the respective electrode surfaces extends beyond the side of the elevated portion.

17. The multielectrode of claim 12, wherein the carrier further includes recesses into which each of the respective electrode surfaces are fitted.

18. The multielectrode of claim 17, wherein at least one of the electrode surfaces extend on the sides of the recesses.

19. The multielectrode of claim 17, wherein each recess is delimited by vertical edges elevated from the carrier, thereby preventing short-circuiting between adjacent electrode surfaces.

20. The multielectrode of claim 12, wherein the carrier further includes electrically conductive material that is attached to at least one of the electrode surfaces.

21. The multielectrode of claim 12, wherein the carrier further includes an adhesive for attaching the multielectrode to the detection site.

22. The multielectrode of claim 12, wherein the carrier is formed using a plurality of thin insulating layers, wherein the respective electrode surfaces are included within the plurality of thin insulating layers, and at least a portion of each respective electrode surface extends beyond the plurality of thin insulating layers.

23. A method for measuring a low amplitude bioelectrical signal at a detection site, the method comprising:

receiving the low amplitude bioelectrical signal using at least one active electrode surface and at least a first reference electrode surface, wherein the low amplitude bioelectrical signal is received in response to an applied bioelectrical stimulus signal;

determining an evoked first bioelectrical potential difference a plurality of times, wherein the evoked first bioelectrical potential difference is based upon the low amplitude bioelectrical signal received using the at least one active electrode surface and the first reference electrode surface;

receiving the low amplitude bioelectrical signal using the at least one active electrode surface and at least a second reference electrode surface, wherein the low amplitude bioelectrical signal is received in response to the applied bioelectrical stimulus signal;

determining an evoked second bioelectrical potential difference a plurality of times, wherein the evoked second bioelectrical potential difference is based upon the low amplitude bioelectrical signal received using the least one active electrode surface and the second reference electrode surface;

amplifying and filtering the plurality of first bioelectrical potential differences;

amplifying and filtering the plurality of second bioelectrical potential differences; and summing the plurality of evoked first bioelectrical potential differences and the plurality of evoked second bioelectrical potential differences in order to increase the signal-to-noise ratio of the low amplitude bioelectrical signal.

24. The method of claim 23, further comprising:

recording the first bioelectrical potential differences after a predetermined time delay, wherein the predetermined time delay is the period of time that the bioelectric stimulus signal is applied.

25. The method of claim 23, further comprising:

inverting at least one of the plurality of first bioelectrical potential differences recorded.

26. The method of claim 23, further comprising:

recording the second bioelectrical potential differences after a predetermined time delay, the predetermined time delay being the period of time that the bioelectric stimulus signal is applied.

27. The method of claim 23, further comprising:

inverting at least one of the plurality of second bioelectrical potential differences recorded.

* * * * *